United States Patent [19]

Luck et al.

[11] Patent Number: 4,978,332
[45] Date of Patent: * Dec. 18, 1990

[54] TREATMENTS EMPLOYING VASOCONSTRICTIVE SUBSTANCES IN COMBINATION WITH CYTOTOXIC AGENTS FOR INTRODUCTION INTO CELLULAR LESION AREAS

[75] Inventors: Edward E. Luck; Dennis M. Brown, both of Menlo Park, Calif.

[73] Assignee: Matrix Pharmaceutical, Inc., Menlo Park, Calif.

[*] Notice: The portion of the term of this patent subsequent to Oct. 28, 2003 has been disclaimed.

[21] Appl. No.: 101,599

[22] Filed: Sep. 28, 1987

[51] Int. Cl.$^5$ .............................................. A61N 1/30
[52] U.S. Cl. ...................................... 604/19; 514/930
[58] Field of Search ............... 604/890.1, 890.2, 20, 604/46, 19; 514/801, 802, 930, 2; 424/450; 128/897, 898

[56] References Cited

U.S. PATENT DOCUMENTS

| | | | |
|---|---|---|---|
| 3,238,101 | 3/1966 | Fruhstorfer et al. | 514/930 |
| 3,993,754 | 11/1976 | Rahman | 424/450 |
| 4,177,263 | 12/1979 | Rosenberg et al. | 514/492 |
| 4,186,183 | 1/1980 | Steck et al. | 424/450 |
| 4,372,949 | 2/1983 | Kodama | 424/450 |
| 4,536,387 | 8/1985 | Sakamoto et al. | 514/781 |
| 4,558,690 | 12/1985 | Joyce | 128/1 R |
| 4,619,913 | 10/1986 | Luck et al. | 514/802 |
| 4,710,493 | 12/1987 | Landsberger | 514/56 |
| 4,738,955 | 4/1988 | Landsberger | 514/56 |

OTHER PUBLICATIONS

Krementz, et al., "Hyperthermic Regional Perfusion for Melanoma of the Limbs", *Cutaneous Metanoma:* Chapter 10, 1985, pp. 171–195.

Yatvin et al., "Design of Liposomes for Enhanced Local Release of Drugs by Hyperthermia", Science, vol. 202, 22, Dec. 1978, pp. 1290–1293.

Maugh, "Bound to Provoke a Reaction", *Science,* vol. 212, pp. 1128–1129, 1981.

Macek et al., *Abstracts of Immunology,* 4109, p. 1053.

Miyata et al., *Cancer Research,* vol. 43, pp. 4670–4675, Oct. 1983.

McLaughlin et al., *Cancer Research, vol. 38, pp. 1311–1316, May, 1978.*

Bier et al., *Cancer,* vol. 44, No. 4, pp. 1194–1200, Oct. 1979.

Primary Examiner—John D. Yasko
Assistant Examiner—Sharon Rose
Attorney, Agent, or Firm—Bertram I. Rowland

[57] ABSTRACT

A pharmaceutical composition and method of treating cellular disorders involving abnormal solid cellular growths which comprises administering a pharmaceutical composition containing cytotoxic agents in combination with a vasoconstrictive drug. Enhanced effectiveness of the composition is observed, with reduced cytotoxic effects on cells distant from the site of introduction. Agents may be included to enhance therapeutic gain and reduce adverse affects to normal tissue.

20 Claims, No Drawings

TREATMENTS EMPLOYING VASOCONSTRICTIVE SUBSTANCES IN COMBINATION WITH CYTOTOXIC AGENTS FOR INTRODUCTION INTO CELLULAR LESION AREAS

BACKGROUND OF THE INVENTION

1. Field of the Invention

The treatment of many cellular disorders, for example, tumors, and hyperproliferative disease, e.g. psoriasis, involves the use of cytotoxic drugs. These drugs exert their activity in a variety of ways, usually interfering with a cellular function essential for the replication and/or viability of the cell. In many, if not most instances, the drug is not specific for the abnormal cell, but rather tends to exert its effectiveness due to the more rapid proliferation of the abnormal cell, as compared to normal cells. While many organs of the body of a mammalian host regenerate cells rather slowly, there are also other organs, particularly bone marrow, which involve rapid proliferation of stem cells. Therefore, the cytotoxic agents not only can detrimentally affect the slowly regenerating cells, but also have a particularly pernicious effect on the immune system.

Despite the many disadvantages and side effects of employing the strongly cytotoxic drugs, they have found extensive application because they have provided positive results. However, there is substantial interest in being able to employ the drugs in a manner which directs their activity toward the abnormal cells, while simultaneously protecting sensitive normal cells, both in the vicinity of and distant from the site of application.

RELEVANT LITERATURE

U.S. Pat. Nos. 4,322,398, 4,347,234, 4,349,530, 4,391,797 and 4,536,387 describe implants and controlled release of drugs. Implantation of drugs in lesions is described in Maugh, *Science* (1981) 212:1128–1129: Macek et al., *Abstracts of Immunology,* 109, p. 1053: Miyata et al. *Cancer Research* (1983) 43:4670–4675: McLaughlin et al. *Cancer Research* (1978) 38:1311–1316: and Bier et al. *Cancer* (1979) 44:1194–1200. U.S. Pat. No. 4,619,913 describes the use of cytotoxic drugs and vasoconstrictive drugs in a proteinaceous matrix. See also references cited therein.

SUMMARY OF THE INVENTION

Abnormal solid cellular growth, particularly tumors or adjacent tissue that may contain tumor cells, and other hyperproliferative conditions, are treated by subjecting the abnormal growth area or tissue suspected of containing tumor cells to a pharmaceutically effective amount of a combination of a cytotoxic drug and a vasoconstrictive drug. The combination substantially inhibits migration of the cytotoxic drug from the site of application by alteration of the blood flow serving the tumor/lesion area, so as to maintain the primary effect of the cytotoxic drug at the site of application.

DESCRIPTION OF THE SPECIFIC EMBODIMENTS

Compositions and methods are provided for the chemotherapeutic treatment of solid tumors, abnormal cellular growth, hyperproliferative conditions, or adjacent tissues which may contain abnormal tumor cells. The treatment may be employed with various solid tumors, including carcinomas, lymphomas and sarcomas. The chemotherapeutic compositions comprise an antiproliferative or cytotoxic drug and a vasoconstrictive drug. The drug combination is applied at the region of the lesion either intralesionally by injection or adjacent to or at the surface of the lesion, conveniently by means of a catheter.

It will be understood that the term cytotoxic refers to any anti-neoplastic or anti-proliferative agent. It will also be understood that the term vasoconstrictive refers to any agent which constricts capillaries so as to substantially restrict the flow of blood to or through the blood vessel. By employing the subject combination, the circulating blood level of the cytotoxic drug remains low. In this way, an enhanced therapeutic gain is achieved, that is, the cytotoxic effect on the treated neoplastic cells is greater as compared to susceptible normal cells remote from the application site.

Hyperproliferative growth means a preneoplastic lesion or condition such as psoriasis, keloids, or warts. It will be understood that the terms neoplastic and neoplastic lesion refer to any new or abnormal growth, such as: cancer, oncogenically transformed cells, carcinomas, melanomas, lymphomas, myelomas, both benign and malignant tumors, and sarcomas.

Illustrative of the various diseased states or therapeutic modes in which the subject invention may find application are: (1) Neoplasms in which local recurrence is typical and drug bioavailability is compromised, e.g., brain: (2) tumors in which suspected neoplastic cells remain in the tumor bed following surgical resection, e.g., breast: (3) tumors which are poor candidates for surgical or radiation management, e.g., head, neck, prostrate, etc.; (4) adjunctive tumor therapy in combination with physical or non-chemical treatments, e.g., radiation and/or hyperthermia: (5) hyperproliferative diseases refractory to conventional therapy, e.g., psoriasis: (6) concurrent treatment with systemic chemotherapy: and (7) concurrent with systemic rescue, e.g. intravenous leucovorin.

In some instances it may be desirable to include non-proteinaceous carriers, so as to form a liquid, particularly aqueous, or semi-solid or gel medium. Compositions which may find use are physiologically acceptable substances, such as carbohydrates, polylactate, agaroses, dextrans, cellulose, gums, etc. Synthetic peptides may find use, such as polylysine, polyarginine, etc. The composition may be formulated with lipids to form liposomes or in a solid form in combination with silicones, epoxide resins, hydroxyapatite, etc. The drugs and carrier will be selected to minimize any inactivating effects on the drugs.

Various drugs may be employed which are used in chemotherapy and act as alkylating agents, enzyme inhibitors, proliferation inhibitors, lytic agents, DNA synthesis inhibitors, membrane permeability modifiers, DNA intercalators, antimetabolites, or the like. Illustrative drugs include: cisplatin (Platinol), doxorubicin hydrochloride (Adriamycin), bleomycin sulfate (Blenoxane), fluorouracil, vincristine sulfate (Oncovin), vinblastine sulfate (Velban) VP-16, chlorambucil (Leukeran), melphalan (Alkeran), busulfan (Myleran), carmustine [BCNU] (BiCNU), lomustine [CCNU] (CeeNU), streptozotocin, thiotepa, dacarbazine (DTICDOME), methotrexate, cytarabine (Cytosar-U), azaribine, mercaptopurine (Purinethol), thioguanine, actinomycin D, plicamycin (Mithracin), mitomycin-C (Mutamycin), asparaginase MSD (Elspar), procarbazine hydrochloride (Matulane), prednisone, prednisilone, triamcinolone, testosterone, estrogen, insulins, and hydroxyurea (Hydrea). Other drugs of interest include radiosensitizers, such as SR-2508 and misonidazole: hyperthermia sensitizers, such as lidocaine and marcaine: bioreductive agents, such as mitomycinc benzotriazine dioxides and nitroheterocyclic compounds such as benznidazole. See Carter and Livingston, Drugs Available to Treat Cancer, In Principles of Cancer Treatment (Carter et al., eds.) Chapter 10, pp. 111-145, 1982, McGraw-Hill, Inc., N.Y.

The drugs may be used individually or in combination, depending upon the nature of the drug, the tumor, and whether cooperative action is pharmacologically indicated. The drug composition can be further modified, by modifying the drug, particularly by bonds which allow for enzymatic cleavage, e.g., hydrolysis, or by introducing materials into the composition which will further aid in the maintenance of the retention of the drug at the site of introduction.

Illustrative vasoconstrictive agents are: (1) sympathomimetics including the catecholamines, norepinephrine, epinephrine, isoproterenol, dopamine, and related compounds such as ephedrine and other phenylisopropylamines, phenylephrine, amphetamine, metraminol, methoxamine: (2) ergot alkaloids including lysergic acid, lysergic acid diethylamine, ergonovine, methylergonavine, methysergide, ergotamine: (3) the angiotensins: and (4) the prostaglandins. Vasoconstrictive agents are described in *Medical Pharmacology* (1984), C. V. Mosby, Company, Chapter 15.

For enhancing cytotoxicity, other agents such as those affecting tissue architecture may be used. These include enzymes which can injure the stroma, such as the peptidases papain, chymopapain, trypsin, amylase, collagenase and chymotrypsin. Similarly, agents affecting cellular permeability may be employed, such as anionic, cationic or non-ionic detergents, e.g., Tween 80, amphotericin B, dimethylsulfoxide. Anaesthetics, such as procaine, may be included in the formulations. Also, other agents which overcome inherent cellular drug resistance, like verapamil, may be included.

In addition, the drug(s) can be employed encapsulated in liposomes or other controlled rate release compositions so as to provide for separate and distinct rates of release of the drug. In this way, multiphasic compositions can be prepared, so as to provide for sustained release of the drug over long periods of time. Formation of liposomes with inclusion of various materials is described in Papahadjopoulos (1978) Annals of the N.Y. Academy of Science, 308: Gregoriadis and Allison (1980) Liposomes in Biological Systems, John Wiley and Sons, Leserman et al., *Nature* (1981) 293:226-228: Barhet et al., *Supramol. Struct. Cell. Bio. Chem.* (1981) 16:243-258: and Heath et al., *Science* (1980) 255:8015-8018. Alternatively, other methods of encapsulation can be employed where the drug is encapsulated in a biodegradable substance, where the rate of release is related to the thickness of the biodegradable coat.

For enhancing cytotoxic activity, various adjuvant materials may be incorporated into the pharmaceutical composition, such as radioactive pellets, e.g., radionuclides technicium or iridium; radiation sensitizers, e.g., nitroimidazoles and halogenated pyrimidines (BUdR): repair inhibitors, e.g., methylated xanthines: bioreductive agents, which are activated only in hypoxic cells; cytokines, such as the interferons, lymphokines, such as interleukin-2: tumor growth inhibitors, such as tumor necrosis factor, transforming growth factor-$\beta$, etc. Angiographic contrast media may also be incorporated into the composition to facilitate visualization.

Other materials as well may be included to enhance an immunogenic cytotoxic response, e.g., proliferation and invasion of macrophage, helper T-cells, etc. Illustrative adjuvants include *Corynebacterium parvum, Bacillus Calmette-Guerin* cell wall or cell wall skeleton preparations, *Mycobacterium bovis* strain, etc. See Miyata et al., *Cancer Res.* (1983) 43:4670-4675: Bier et al. *Arch. Otorhinolaryngol.* (1982) 236:245-255: and Mehanijhlin et al., *Cancer Res.* (1978) 38:1311-1316, whose relevant disclosure is incorporated herein by reference.

The pharmaceutical composition of this invention may be uniformly dispersed in a physiologically acceptable medium, particularly aqueous, such as saline, phosphate buffered saline, distilled water, etc. The aqueous medium will be sufficient to provide for an amorphous dispersion, usually a solution, capable of flowing under mild pressure. Usually, the liquid aqueous medium will be at least 5 weight percent of the entire composition, more usually at least 10 weight percent, and not more than about 75 weight percent, usually not more than about 50 weight percent, so as to provide a flowable mixture. The amount will vary depending upon the nature of the drug(s), the nature of any carrier material, the presence of other materials, and the like. The concentration of protein other than carrier protein in the aqueous medium, if any, will range from about 0 to 75 mg/ml.

The cytotoxic drug(s) will normally be a liquid or solid, or provided in a flowable dispersed form and will generally range from at least about 0.1% by weight up to about 50% by weight, more usually being from about 1% to 50% by weight of the formulation. The vasoconstrictive agent(s) will generally be present in about 0.5 to 35, usually 5 to 20 weight percent of the formulation.

Other ancillary additives or agents as described above may be present and will vary in total amount from about 0.005 to 15 weight percent, usually from about 0.01 to 10 weight percent of the total composition.

In addition to the cytotoxic drugs and vasoconstrictors, a number of minor components may also be included for a variety of purposes. These agents will or the most part impart properties which protect the stability of the composition, control the pH, or the like. Illustrative agents include phosphate or acetate buffers, methyl or propyl paraben, polyethylene glycols, etc. These agents generally will be present in less than about 2 weight percent of the total composition, usually less than about 1 weight percent, and individually may vary from about 0.001 weight percent to about 1 weight percent.

As already indicated, in some instances the drug will be encapsulated particularly in liposomes. Liposomes are prepared from a variety of lamellar-forming lipids including phospholipids, e.g., phosphatidylcholine, phosphatidylethanolamine, etc., gangliosides, sphingomyelins, steroids, e.g., cholesterol, etc. Usually, the weight of the lipids in relation to the weight of drug will range from 1 to 5 liters of entrapped drug per mole of amphipathic lipid.

The pharmaceutical composition of the present invention can be prepared by combining the various components in a sterile environment. The composition will be provided in a convenient form, usually admixed with at least a portion of the total aqueous medium to be employed. The composition will be sufficiently workable so that, upon admixture of the other agents, a uniform dispersion can be obtained.

Other materials, as appropriate, may be added concomitantly or sequentially. After ensuring the uniform dispersion of the various components in the mixture, the mixture may be sterilized and sealed in an appropriate container. In the event the various components are unstable or form undesirable complexes when stored in a mixture prior to administration, each component may be dispensed at an appropriate concentration into a separate container for mixing just prior to administration. Those components which are stable together may be dispensed together into a single container for mixture with one or more reagents containing those additional ingredients found to promote instability or to form undesirable complexes. A device or kit containing separate components may be prepared which facilitates easy formulation prior to administration. The concentration of each separate component is formulated so that the therapeutically effective concentration of each agent is achieved when all the separate components in the kit are admixed.

The composition of this invention can be used in the treatment of a wide variety of neoplastic or benign lesions. Illustrative tumors include carcinomas, sarcomas and melanomas, such as basal cell carcinoma, squamous cell carcinoma, melanomas, soft tissue sarcoma, solar keratoses, Kaposi's sarcoma, cutaneous malignant lymphoma, Bowen's disease, Wilm's tumor, hepatomas, colorectal cancer, brain tumors, mycosis fungoides, Hodgkins lymphoma, polycythemia vera, lymphomas, oat cell sarcoma, etc. Also subject to treatment are warts, benign lesions, preneoplastic lesions, and hyperproliferative diseases, such as psoriasis.

The composition of this invention will be administered to a tumor to provide a cytotoxic amount of drug at the tumor site. The amount of cytotoxic drug administered to the tumor site will generally range from about 0.1 to 500, more usually about 0.5 to 300 mg/kg of host, depending upon the nature of the drug, size of tumor, and other considerations.

In view of the wide diversity of tumors, nature of tumors, effective concentrations of drug, relative mobility and the like, a definitive amount for administration cannot be specified. With each drug in each tumor, experience will provide an optimum level. One or more administrations may be employed, depending upon the lifetime of the drug at the tumor site and the response of the tumor to the drug. Administration may be by syringe, catheter or other convenient means allowing for application of a flowable composition at the tumor site. Administration may be every third day, weekly, or less frequent, such as biweekly or at monthly intervals.

Injection may be at one or more sites depending on the size of the lesion. Needles of about 1-2 mm diameter are convenient. For multiple injection, templates with predrilled holes may be employed.

The method of the present invention finds particular advantage with tumors or lesions which are clinically relevant. The compositions provided show particular therapeutic gain with tumors greater than 100 mm$^3$, more particularly, greater than 150 mm$^3$, in volume, as well as flat cutaneous lesions with surface areas ranging from 10 mm$^2$ to 100 cm$^2$ or greater.

The method of the present invention also reduces local inflammation as a result of drug administration, therefore, local or adjacent tissue is less likely to be affected by the drug. Furthermore, due to the low migratory level of the drug from the site of placement, higher drug dosages can be administered to the site without adverse affects to normal tissue distant from the placement site or to lymphocytes.

The method of the present invention finds advantage in conjunction with other forms of therapy. The lesions may be irradiated prior and/or subsequent to drug administration. Dose rates may vary from about 20 to 250 rad/min, usually 50 to 150 rad/min, depending on the lesion, period of exposure, and the like. Hyperthermia (heat) may be used as an adjunctive treatment. Treatment will usually involve heating up of the tissue to be treated to about and including 43° C. for about 5 to 100 min.

In order to demonstrate the subject invention the following investigations were performed. The following experiments are illustrative of various embodiments of the invention, but do not in any way limit it.

The transplantable experimental murine fibrosarcomas RIF-1 or KHT were grown intradermally ($2 \times 10^5$ cells injected i.d.) in the flank of 5 month old male C3H mice. When tumors reached a volume of ~100 mm$^3$ they were used for the studies. The cytotoxic drugs under study (all were formulated for human clinical use) were made up just prior to use in their appropriate aqueous vehicle except those experimental groups in which epinephrine-HCl (1 mg/ml) was added to the aqueous drug (usually ~10% of total volume). Drug concentrations were: adriamycin, 3.75 mg/ml: BCNU, 10 mg/ml: vinblastine, 1.2 mg/ml; and 5-fluorouracil, 30 mg/ml. The drugs were administered intraperitoneally (i.p.) or intratumorally (i.t.) in an injection volume of 0.1 ml. The tumors of the treated mice as well as untreated control tumors were measured three times per week by vernier calipers and their volumes were calculated by the formula:

$$V = \pi/6 \times D_1 \times D_2 \times D_3$$

where $D_1$-$D_3$ are tumor diameters in mm. The time (days) for the tumors to grow to four times their original experimental volume was used as a parameter of treatment effectiveness. Epinephrine in the doses used (1 mg/kg) was not chemotherapeutic when used alone. The data for the drugs studied is summarized in Table 1.

Further evidence for the demonstration of the enhancement of localized tumor concentration of chemotherapy drugs in combination with a vasoconstrictive agent (such as epinephrine) compared to the tumor concentration of the chemotherapeutic agent used alone is demonstrated in Table 2. In this experiment, mice bearing the RIF-1 fibrosarcomas are injected Table 1
Influence of Epinephrine (1 mg/kg) (Epi) In Combination with Anticancer Drugs Administered Intratumorally (i.t.) on the Growth of Murine Fibrosarcomas

| Drug | Dose (mg/kg BW) | Route of Administration | Tumor | Tumor Growth Ratio* |
|---|---|---|---|---|
| Adriamycin | 15 | i.p. | RIF-1 | 1.63 |
| Adriamycin | 15 | i.t. | RIF-1 | 3.04 |
| Adriamycin + Epi | 15 | i.t. | RIF-1 | 3.24 |
| 5-Fluorouracil | 100 | i.p. | RIF-1 | 1.20 |

Table 1-continued

Influence of Epinephrine (1 mg/kg) (Epi) In Combination with Anticancer Drugs Administered Intratumorally (i.t.) on the Growth of Murine Fibrosarcomas

| Drug | Dose (mg/kg BW) | Route of Administration | Tumor | Tumor Growth Ratio* |
|---|---|---|---|---|
| 5-Fluorouracil | 100 | i.t. | RIF-1 | 1.30 |
| 5-Fluorouracil + Epi | 100 | i.t. | RIF-1 | 1.44 |
| Vinblastine | 2 | i.p. | KHT | 1.16 |
| Vinblastine | 2 | i.t. | KHT | 1.76 |
| Vinblastine + Epi | 2 | i.t. | KHT | 2.92 |
| Vinblastine | 2 | i.p. | RIF-1 | 1.12 |
| Vinblastine | 2 | i.t. | RIF-1 | 3.01 |
| Vinblastine + Epi | 2 | i.t. | RIF-1 | 4.00 |
| BCNU (carmustine) | 40 | i.t. | KHT | 2.08 |
| BCNU + Epi | 40 | i.t. | KHT | 2.80 |

*This ratio indicated the time it would take a treated tumor to grow to 4× its initial size, divided by the time it would take an untreated tumor to grow to 4× its initial size. For example, if it took a treated tumor 40 days to grow from 100 mm$^3$ to 400 mm$^3$, and an untreated tumor 10 days to grow from 100 mm$^3$ to 400 mm$^3$; this would give us a tumor growth ratio of 4.0. Thus, increasing ratios indicate improved treatment effectiveness.

TABLE 2

Influence of Epinephrine (Epi) (0.5 mg/Kg) on Intratumoral Delivery of 5-FU: Ratios of Tumor to Plasma Concentration and Ratios of 5-FU Concentration ± Epi in RIF-1 Tumor

| Time Post Injection (Hours) | 5-FU Tumor/Plasma Ratio | | Tumor (5-FU + Epi, i.t.) / Tumor (5-FU, i.t.) |
|---|---|---|---|
| | 5-FU, i.t. | 5-FU + Epi, i.t. | |
| 0.5 | 24.59 | 198.34 | 4.94 |
| 1.0 | 14.63 | 137.42 | 5.04 |
| 2.0 | 47.53 | 82.35 | 1.68 |
| 4.0 | 19.01 | 58.46 | 2.24 |
| 24.0 | 4.10 | 6.57 | 1.48 | intratumorally (i.t.) with 0.1 ml of an aqueous solution of tritium labeled 5-fluorouracil (5-FU) (25 μCi/ml stock solution, Amersham), or an equivalently radioactively labeled solution of 5-FU that also contains epinephrine at a final concentration of 2.5 mg/ml. Plasma and tumor samples were taken 0.5, 1, 2, 4 and 24 hours after injection. The tissues were solubilized in Scintigest (Fisher Scientific), corrected for their tissue weight, and 200 μl of the solubilized samples were added to 6 ml of scintillation fluid and counted in a liquid scintillation counter for the presence of tritium. The values in Table 2 are ratios of the normalized counts (based on 100 mg of tissue, wet weight) in tumor divided by the radioactivity in the plasma samples. The data demonstrate that at every time point evaluated, a 1.48 to 5.04 enhancement of 5-FU tumor concentration to plasma concentration was observed when epinephrine was included in the 5-FU. This indicates that the vasoconstrictive activity of epinephrine promotes the localization and retention of the drug in the tumor and limits the diffusion of the cytotoxic agent from the tumor into systemic circulation (i.e. low plasma drug concentrations).

Thus, it can be seen that improved neoplastic therapy is achieved by applying to a neoplastic lesion a composition comprising a cytotoxic drug in combination with a vasoconstrictive agent. It is found that by employing the drug composition, greatly enhanced localized drug concentration can be achieved. In addition, in view of the significant cytotoxic effects of drugs employed in chemotherapy, systemic exposure is substantially diminished. Therefore, higher levels of cytotoxic drugs can be employed at the site of interest, while the remainder of the host is not exposed to significant levels of the drug.

Although the foregoing invention has been described in some detail by way of illustration and example for purposes of clarity of understanding, it will be obvious that certain changes and modifications may be practiced within the scope of the appended claims.

What is claimed is:

1. A method for treating a neoplastic lesion or surrounding tissue which comprises:
   applying at the site of said length a composition consisting essentially of a uniformly dispersed vasconstrictive drug and at least one uniformly dispersed cytotoxic drug in a non-proteinaceous aqueous medium;
   whereby said drug is retained in the immediate environment avoiding significant levels of the drug at sites distant from the site of introduction.

2. A method according to claim 1, wherein said vasoconstrictive drug is at least one of the following: epinephrine, norepinephrine, the catecholamines, epinephrine isoproterenol, dopamine, ephedrine, phenylephrine, amphetamine, metraminol, methoxamine, ergot alkaloids, ergonovine, methylergonavine, methysergide, ergotamine, an angiotensin, and a prostaglandin: said vasoconstrictive drug present in a therapeutically effective amount.

3. A method according to claim 1, wherein said cytotoxic drug is at least one of the following: an alkylating agent, enzyme inhibitor, lytic agent, DNA synthesis inhibitor, membrane permeability modifier, DNA intercalator, or antimetabolite.

4. A method according to claim 1, wherein said cytotoxic drug is at least one of the following: cisplatin, doxorubicin hydrochloride, bleomycin sulfate, fluorouracil, vincristine sulfate, vinblastine sulfate, chlorambucil, melphalan, busulfan, carmustine, lomustine, streptozotocin, thiotepa, dacarbazine, methotrexate, cytarabine, azaribine, mercaptopurine, thioguanine, actinomycin D, plicamycin, mitomycin-C, asparaginase, procarbazine hydrochloride, prednisone, prednisi iamcinolone, testosterone, estrogen, insulin, BUdR nitrosourea, hydroxyurea.

5. A method according to claim 1, wherein said composition in addition consists of an agent affecting tissue architecture and present in a therapeutically effective amount.

6. A method according to claim 5, wherein said agent affecting tissue architecture is at least one of papain, chymopapain, trypsin, amylase, collagenase and chymotrypsin.

7. A method according to claim 1, wherein said composition in addition consists of an agent affecting cellular permeability and present in a therapeutically effective amount.

8. A method according to claim 7, wherein said agent affecting cellular permeability is at least one of detergents, amphotericin B and dimethylsulfoxide.

9. A method according to claim 1, wherein an affecting cytotoxic activity which is at least one of radionuclides technicium or iridium, misonidazole and cytokines is present in said medium in a therapeutically effective amount.

10. A method according to claim 1, comprising the additional step of treating said lesion site with radiation or heat applied in a therapeutically effective amount.

11. A pharmaceutical composition consisting essentially of a vasoconstrictive drug, a cytotoxic drug and a protein-free aqueous pharmacologically acceptable vehicle.

12. A pharmaceutical composition according to claim 11, wherein said vasoconstrictive drug is at least one of the following: epinephrine, norepinephrine, the catecholamines, epinephrine isoproterenol, dopamine, ephedrine and other phenylisopropylamines, phenylephrine, amphetamine, metraminol, methoxamine, ergot alkaloids, ergonovine, methylergonavine, methysergide, ergotamine, the angiotensins and the prostaglandins.

13. A pharmaceutical composition according to claim 11, wherein said cytotoxic drug is at least one of the following: an alkylating agent, enzyme inhibitor, lytic agent, DNA synthesis inhibitor, DNA intercalator, or antimetabolite.

14. A pharmaceutical composition according to claim 11, wherein said cytotoxic drug is at least one of the following: cisplatin, doxorubicin hydrochloride, bleomycin sulfate, fluorouracil, vincristine sulfate, vinblastine sulfate, chlorambucil, melphalan, busulfan carmustine, lomustine, streptozotocin, thiotepa, dacarbazine, methotrexate, cytarabine, azaribine, mercaptopurine, thioguanine, actinomycin D, plicamycin, mitomycin-C, asparaginase, procarbazine hydrochloride, prednisone, prednisilone, triamcinolone, testosterone, estrogen, insulin, BUdR, nitrosourea, carmustine, lomustine, and hydroxyurea.

15. A pharmaceutical composition according to claim 11, in addition consisting of an agent affecting tissue architecture and present in a therapeutically effective amount.

16. A pharmaceutical composition according to claim 15, wherein said agent affecting tissue architecture is at least one of papain, chymopapain, trypsin, amylase, collagenase and chymotrypsin.

17. A pharmaceutical composition according to claim 11, in addition consisting of an agent affecting cellular permeability and present in a therapeutically effective amount.

18. A pharmaceutical composition according to claim 17, wherein said agent affecting cellular permeability is at least one of detergents, amphotericin B and dimethylsulfoxide.

19. A pharmaceutical composition according to claim 11, in addition consisting of an agent affecting said cytotoxic activity and present in a therapeutically effective amount.

20. A pharmaceutical composition according to claim 19, wherein said agent affecting cytotoxic activity is at least one of radionuclides technicium or iridium, nitroimidazoles, and cytokines.

* * * * *